US00PP23603P3

(12) United States Plant Patent
Olesen

(10) Patent No.: US PP23,603 P3
(45) Date of Patent: May 21, 2013

(54) MINIATURE ROSE PLANT NAMED 'POULPAR056'

(50) Latin Name: *Rosa hybrida*
Varietal Denomination: Poulpar056

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 8 days.

(21) Appl. No.: 13/317,261

(22) Filed: Oct. 13, 2011

(65) Prior Publication Data

US 2013/0097749 P1 Apr. 18, 2013

(51) Int. Cl.
*A01H 5/00* (2006.01)

(52) U.S. Cl.
USPC ..... Plt./120

(58) Field of Classification Search
USPC ..... Plt./120
See application file for complete search history.

*Primary Examiner* — Kent L Bell

(57) ABSTRACT

A new miniature rose plant that has abundant, pink apricot blend flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa hybrida.*
Variety denomination: 'Poulpar056'.

SUMMARY OF THE INVENTION

The present invention constitutes a new and distinct variety of miniature rose plant which originated from a controlled crossing between the female seed parent, an unnamed seedling, and the male pollen parent, an unnamed seedling.

The two parents were crossed during the summer of 2005 and the resulting seeds were planted in a controlled environment in Fredensborg, Denmark. The new variety, named 'Poulpar056', originated as a single seedling from the stated cross.

The new variety may be distinguished from its female seed parent primarily by flower color. The female seed parent has pink flowers while the new variety has pink apricot blended flowers.

The new variety may be distinguished from its male pollen parent primarily by flower color. The male parent has apricot flowers while the new variety has pink apricot blended flowers.

The objective of the hybridization of this rose variety for commercial culture was to create a new and distinct variety with unique qualities, such as:

1. Uniform and abundant pink apricot blend flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpar056' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpar056' was selected by the inventor as a single plant from the progeny of the hybridization in 2005.

Asexual reproduction of 'Poulpar056' by cuttings and traditional budding was first done by Mogens N. Olesen in the nursery in Fredensborg, Denmark in June 2006. This initial and other subsequent propagations conducted in controlled environments have demonstrated that the characteristics of 'Poulpar056' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers, leaves, and stems of 'Poulpar056'.

DETAILED DESCRIPTION OF THE VARIETY

The following is a description of 'Poulpar056', as observed in its growth in glasshouses in Half Moon Bay, Calif. Observed plants are 12 weeks of age and were cultivated in 10.5 cm pots. Color references are made using The Royal Horticultural Society (London, England) Colour Chart, 2001, except where common terms of color are used.

For a comparison, several physical characteristics of the rose variety 'Poulpar041', U.S. Plant Pat. No. 17,889. are compared to 'Poulpar056' in Chart 1.

CHART 1

| | 'Poulpar056' | 'Poulpar041' |
|---|---|---|
| Petal color, upper surface | Red Group 51C splashed with intonations of Red Group 52B. | Red Group 37B blended with Orange-Red Group 32C and 32D at the margins. |
| Flower Diameter | 50 to 60 mm | 35 to 40 mm |
| Petal count | 65 petals | 35 petals |

FLOWER AND FLOWER BUD

Blooming habit: Continuous.
Flower bud:
*Size*.—Upon opening, 25 mm in length from base of receptacle to end of bud. 12 mm in diameter.
*Bud form*.—Ovate.
Bud color: As sepals unfold, petals are Red Group 53C.
Sepals:
*Upper surface*.—Color: Yellow-Green Group 147A. Texture: Weak pubescence.
*Lower surface*.—Color: Yellow Green Group 146B. Texture: Smooth.
*Shape*.—Apex: Cirrhose. Base: Flat at union with receptacle.
*Margins*.—Margins have medium foliaceous appendages on three of the five sepals.
*Size*.—35 mm long by 6 mm wide.
Receptacle:
*Surface texture*.—Smooth.
*Shape*.—Funnel shaped.
*Size*.—4 mm in height by 7 mm wide.
*Color*.—Yellow Green Group 144A.
*Pedicel*.—Surface: Few small prickles and stipitate glands. Length: 45 to 50 mm. Diameter: 3 mm. Color: Yellow-Green Group 144A. Strength: Medium strength.
*Borne*.—Singly.
Flower bloom:
*Fragrance*.—Moderate floral scent.
*Duration*.—As a pot plant, flowers last from 21 to 25 days. Petals do not fall cleanly away from plant.
*Size*.—Flower diameter is 50 to 60 mm when open. 25 mm deep.
*Form*.—General shape is a rosette, with many overlapping petals packed into quarter sections.
*Shape of flower, side view*.—The upper portion is flat. The lower portion is convex.
Petalage: There are normally 65 petals, 15 of which are petaloids.
Color:
*Upon opening, petals*.—Outermost petals: Upper Surface: Red Group 51C splashed with intonations of Red Group 52B. Lower Surface: Red Group 52C splashed with intonations of Red Group 54A. Innermost petals: Upper Surface: Red Group 51C splashed with intonations of Red Group 52B. Lower Surface: Red Group 54A.
*Upon opening, basal petal spots*.—Yellow Group 2C on upper and lower surface.
*After opening, petals*.—Outer and inner petals: Upper Surface: Red Group 48B splashed with intonations of Red Group 50B. Lower Surface: Red Group 52C splashed with intonations of Red Group 54A and faintly Yellow-Orange Group 22D.
*After opening, basal petal spots*.—Yellow Group 2C.
General tonality: On open flower Red Group 38A with intonations of Red Group 55B. No change in the general tonality at the end of the 10th day.
Petals:
*Petal reflex*.—Moderately.
*Petal margin*.—Very often, multiple clefts appear at the margin. There are strong undulations in the petal margin.
*Shape*.—Overall broadly elliptic. The apex is emarginate. The base is acute.
*Size*.—On average 30 mm in length by 35 mm wide. Inner petals are 20 mm in length by 15 mm wide.
*Thickness*.—Average.
Petaloids:
*Quantity*.—Normally, there are about 15.
*Size*.—On average 15 mm long; 7 mm wide.
*Shape*.—Symmetric. Apex is rounded. Base is acute.
*Color*.—Upper surface Red Group 48B splashed with intonations of Red Group 50B. Lower surface is Red Group 52C splashed with intonations of Red Group 54A and faintly Yellow-Orange Group 22D. Basal petal spots are Yellow Group 2C on both sides.
Reproductive organs:
*Pollen*.—None observed.
*Anthers*.—Size: 2 mm long. Color: Yellow Group 10B. Quantity: About 40.
*Filaments*.—Color: Yellow Group 11D. Length: 3 mm.
*Pistils*.—Length: 3 mm long. Quantity: About 15.
*Stigmas*.—Level relative to the length of the filaments and the height of the anthers. Color: Orange-White Group 159C.
*Styles*.—Color: Green-White Group 157C and Red Group 43C.
*Seed formation*.—Not observed.

PLANT

Plant growth: Upright. When grown as a 10.5 cm pot on its own roots, the average height of the plant itself is 19 cm and the average width is 15 cm.
Stems:
*Color*.—Young wood: Yellow-Green Group 144B. Older wood: Yellow-Green Group 144A.
*Internodal distance*.—20 mm.
*Length and width*.—From the base of the plant to the flowering portion is 13 cm. The diameter is 3 mm on average.
*Surface texture*.—Young wood: Smooth. Older wood: Smooth.
Prickles: None. Observed plants are without prickles.
Plant foliage: Normal number of leaflets on normal leaves in middle of the stem: 5 leaflets.
*Compound leaf size*.—70 mm (l)×40 mm (w).
*Quantity*.—4 leaves per 10 cm of stem.
*Color*.—
*Juvenile foliage*.—Upper Leaf Surface: Yellow-Green Group 147A to 146B. Lower Leaf Surface: Yellow-Green Group 147C. Anthocyanin: Greyed-Purple Group 183A on the leaflet margins.
*Mature foliage*.—Upper Leaf Surface: Yellow-Green Group 147A. Lower Leaf Surface: Yellow-Green Group 147B.
Plant leaves and leaflets:
*Stipules*.—Size: 10 mm in length. Shape: Linear, slightly broad based with outward extending apices. Margins: Entire. Color: Yellow-Green Group 144A.
*Petiole*.—Length: 13 mm long by 1 mm wide. Color: Upper surface is Yellow-Green Group 144A with anthocyanin the color of Greyed-Purple Group 183B. Lower surface is Yellow-Green Group 144A. Underneath: Small prickles observed.
*Rachis*.—Size: About 25 mm long. Color: Upper surface is Yellow-Green Group 144A with anthocyanin the color of Greyed-Purple Group 183B. Lower surface is Yellow-Green Group 144A. Underneath: Small prickles observed.

*Leaflet*.—Size: Terminal leaflets are 28 mm length by 18 mm wide on average. Margin: Doubly serrate. General Shape: Elliptical. Apex Shape: Acute. Base Shape: Round. Texture: Smooth. Arrangement: Odd pinnate. Venation: Reticulate. Leaf Gloss: Matte finish.

Disease resistance: Average resistance to powdery and downy mildew, black spot, and *Botrytis* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the miniature class named 'Poulpar056', substantially as illustrated and described herein, due to its abundant, pink apricot blend flowers, vigorous growth, compact habit, suitability for production from softwood cuttings in pots, and durable flowers and foliage that make the variety suitable for distribution in the floral industry.

* * * * *

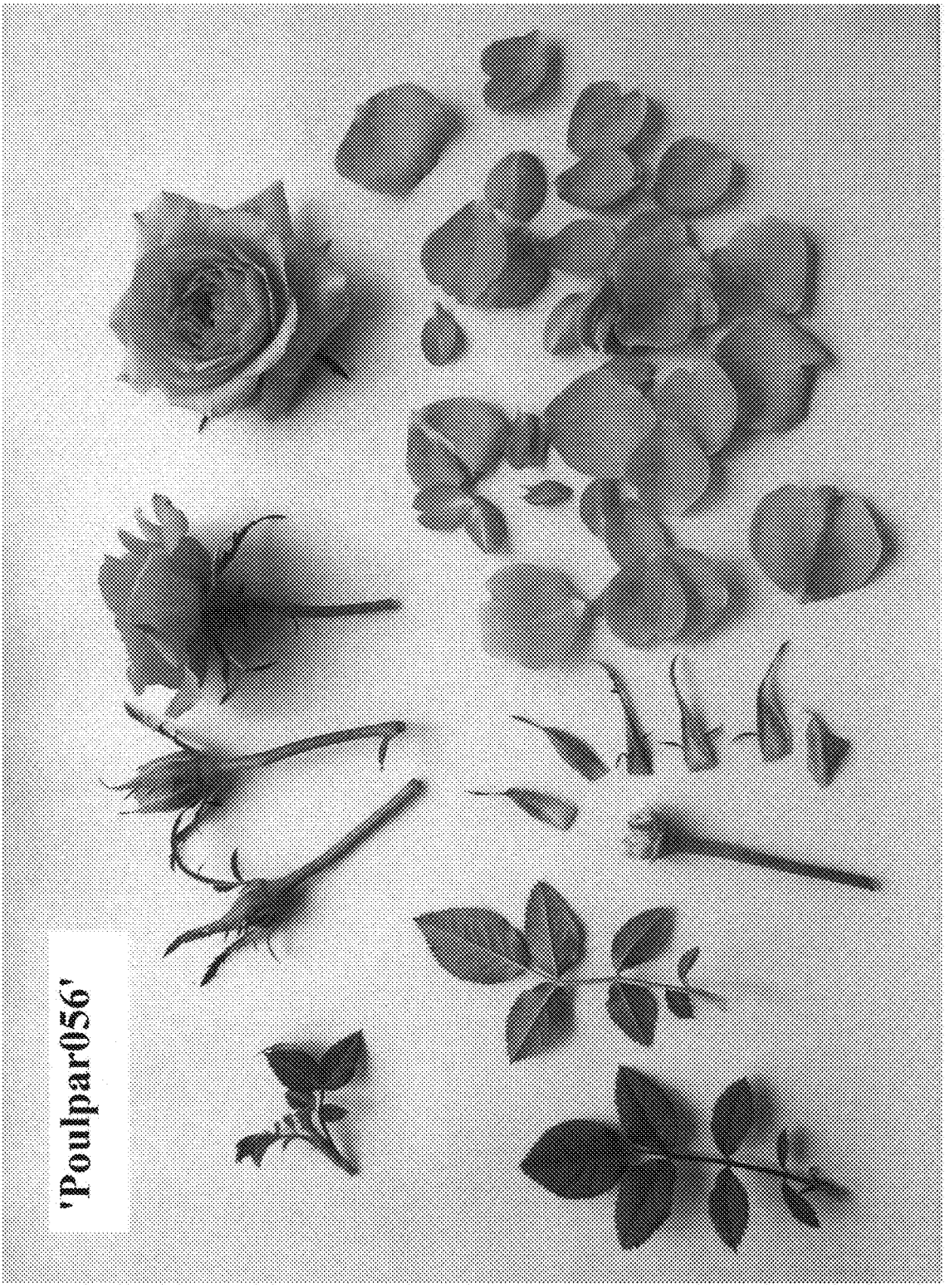
'Poulpar056'